(12) United States Patent
Willemstyn et al.

(10) Patent No.: US 10,206,614 B2
(45) Date of Patent: Feb. 19, 2019

(54) PRE-STERILIZED SYRINGE SYSTEM AND METHOD OF USE

(71) Applicant: PAW BioScience Products, Inc., Eatontown, NJ (US)

(72) Inventors: Benjamin R. Willemstyn, Little Silver, NJ (US); Timothy Korwan, Reading, MA (US)

(73) Assignee: PAW BioScience Products, LLC, Eatontown, NJ (US)

( * ) Notice: Subject to any disclaimer, the term of this patent is extended or adjusted under 35 U.S.C. 154(b) by 321 days.

(21) Appl. No.: 14/991,066

(22) Filed: Jan. 8, 2016

(65) Prior Publication Data
US 2016/0206234 A1 Jul. 21, 2016

Related U.S. Application Data

(60) Provisional application No. 62/105,511, filed on Jan. 20, 2015.

(51) Int. Cl.
*A61B 5/15* (2006.01)
*A61B 50/30* (2016.01)

(52) U.S. Cl.
CPC .... *A61B 5/150992* (2013.01); *A61B 5/15003* (2013.01); *A61B 5/150221* (2013.01); *A61B 5/150236* (2013.01); *A61B 5/150244* (2013.01); *A61B 2050/314* (2016.02)

(58) Field of Classification Search
CPC .......... A61B 5/150992; A61B 5/15003; A61B 5/150221
See application file for complete search history.

(56) References Cited

U.S. PATENT DOCUMENTS

| 2,625,264 | A | | 1/1953 | Edwards et al. |
| 3,747,812 | A | | 7/1973 | Karman et al. |
| 3,937,219 | A | | 2/1976 | Karakashian |
| 4,758,232 | A | * | 7/1988 | Chak .................. A61B 5/15003 600/578 |
| 4,973,310 | A | | 11/1990 | Kosinski |

(Continued)

FOREIGN PATENT DOCUMENTS

WO    WO 1999/37233 A1    7/1999

OTHER PUBLICATIONS

U.S. Appl. No. 62/105,511, filed Jan. 20, 2015.

*Primary Examiner* — Sean Dougherty
*Assistant Examiner* — Nicholas E Kolderman
(74) *Attorney, Agent, or Firm* — Drinker Biddle & Reath LLP

(57) ABSTRACT

A pre-sterilized fluid sampling syringe is provided which includes a locking vacuum syringe, 3-way valve, check valve and thermoplastic inlet tubing capable of both aseptic welding and direct connections. The syringe is assembled with components and rendered sterile in its packaging. The packaging permits manipulation of the syringe by the user such that at time of use a vacuum can be generated in the syringe barrel by pulling and locking the plunger into a fully withdrawn position. By using the check valve and vacuum feature of the sampling system the user of the device has a means of aseptically flushing and obtaining fluid samples from a desired system, typically a bioreactor or other process used in biotechnology and/or pharmaceutical laboratories and manufacturing operations.

6 Claims, 2 Drawing Sheets

(56) References Cited

U.S. PATENT DOCUMENTS

| | | | |
|---|---|---|---|
| 5,332,092 A | 7/1994 | Fischer | |
| 5,947,890 A * | 9/1999 | Spencer | A61M 25/002 |
| | | | 600/3 |
| 5,997,811 A | 12/1999 | Esposito | |
| 5,997,881 A | 12/1999 | Powell et al. | |
| 7,077,826 B1 | 7/2006 | Gray | |
| 2001/0021820 A1 | 9/2001 | Lynn et al. | |
| 2002/0065505 A1* | 5/2002 | Willemstyn | A61M 39/165 |
| | | | 604/408 |
| 2003/0069543 A1 | 4/2003 | Carpenter et al. | |
| 2004/0030294 A1 | 2/2004 | Mahurkar | |
| 2006/0079834 A1* | 4/2006 | Tennican | A61J 1/2096 |
| | | | 604/88 |
| 2013/0345626 A1* | 12/2013 | Tennican | A61M 5/008 |
| | | | 604/89 |

\* cited by examiner

PRE-STERILIZED SYRINGE SYSTEM AND METHOD OF USE

CROSS-REFERENCE TO RELATED APPLICATION

The present application claims priority benefit to a provisional patent application entitled "Pre-Sterilized Syringe System and Method of Use," which was filed on Jan. 20, 2015, and assigned Ser. No. 62/105,511. The entire content of the foregoing provisional patent application is incorporated herein by reference.

BACKGROUND

Technical Field

The present disclosure relates to an advantageous pre-sterilized fluid sampling system for use in connection with aseptic fluid sample collection, e.g., in the bioprocess and biopharmaceutical manufacturing industries, e.g., to obtain fluid samples in cell culture applications. More specifically, the disclosed system/method substantially reduce or eliminate false positives in sterile fluid sampling resulting from known inadequacies in the fundamental design of conventional syringes.

Background Art

Conventional syringe technology is inadequate for sterile fluid sampling applications due, inter alia, to the exposure of the inner surface of the syringe barrel to the non-sterile ambient environment. When used to collect fluid samples, a syringe is actuated by pulling the plunger away from the inlet of the syringe. This causes the plunger to move upwards and away from the fluid inlet of the syringe and in doing so creates a vacuum which causes fluid to be drawn into the syringe. In this manner, fluid entering the syringe comes in contact with the surfaces of the syringe barrel which were previously in communication with the non-sterile ambient environment, thus potentially contaminating the incoming fluid. Additionally, a basic syringe has no means to flush and divert the initially obtained fluid. The initial fluid is almost always residual fluid from a prior sample or simply material sequestered in a dead-leg conduit leading from the device being sampled. In either case, this initial fluid is often not representative of the fluid desired and must be removed prior to obtaining a meaningful/useful fluid sample.

The patent literature includes teachings relevant to the inadequacies noted herein. For example, U.S. Pat. No. 5,997,811 to Esposito teaches a means for encasing a syringe inside a pouch with the inlet fitting of the syringe welded to the pouch such that the syringe body resides inside the pouch and the syringe inlet resides outside the pouch. This method solves some of the problems associated with fluid sampling; however, operation of the syringe whilst in the pouch is cumbersome and manufacture of the device with a specialized fitting-pouch in this way is expensive and fraught with potential integrity issues at the pouch-seal interface.

U.S. Pat. No. 5,332,092 to Fisher similarly describes sealing a syringe inside a pouch; however, the Fisher disclosure provides for the tip of the syringe to pass through the pouch and does not speak to the requirements of fluid sampling, instead focusing on delivery of a material from the syringe.

U.S. Pat. No. 7,077,826 to Gray discusses several designs, including a collapsible bellows or corrugated sheath positioned internally or between the plunger handle and the barrel of the syringe. These designs preserve the sterile field of the inner barrel surface even when the syringe is located in the outside environment. The challenge in utilizing these designs is again the cost of manufacturing exotic accordion structures and the integrity of the seals required to maintain sterility. The other syringe designs taught be Gray incorporate plungers located inside concentric syringe barrels which act like sealed pistons; however, the ability to maintain true aseptic conditions would require further engineering. The use of elastomeric sealing rings discussed in the Gray '826 patent would fail because there is no means to vent air or vacuum displaced between the concentric walls of the syringe when the components are operated.

Despite efforts to date, a need remains to address and overcome inadequacies in conventional syringe technology in an efficient, reliable and cost effective manner. These and other inadequacies associated with conventional syringe technology are addressed and overcome by the systems and methods disclosed herein.

SUMMARY

According to the present disclosure, a sterilely packaged syringe is advantageously vacuum-charged prior to removing the syringe from its sterile packaging pouch. This initial charging operation is generally performed by pulling back on the plunger to create vacuum within the syringe barrel, rotating the plunger handle to engage an internal locking mechanism, and then removing the syringe system from the sterile packaging pouch. Alternative locking techniques may be employed to detachably secure the plunger in the "pulled back" orientation.

By charging a vacuum into the barrel of the syringe within the sterile packaging pouch, the method and system of the present disclosure facilitates desired positioning of the plunger inside the syringe barrel while in an aseptic field, and due to the pre-positioning of the plunger as described herein, contamination of the fluid sample that is ultimately drawn into the syringe is advantageously avoided. Once removed from the sterile packaging, the vacuum created within the barrel of the syringe allows the user to automatically and immediately draw fluid into the syringe body by opening up a conduit between the syringe body and the device being sampled.

In exemplary embodiments of the present disclosure, actuation of the vacuum to acquire a desired fluid sample is accomplished through the use of a 3-way valve without any risk of contamination. However, prior to actuating the 3-way valve, the user of the device can elect to draw fluid through the check valve, thus removing any residual fluid from the system, whether the residual fluid is from a prior sample or simply undesired fluid considered part of a dead-leg in the sampling line. A check valve may be advantageously included in the disclosed syringe system to guarantee flow will only be from the inside of the system to the outside, thereby further maintaining the sterile integrity of the subsequent fluid sample.

Additional features, functions and benefits of the disclosed syringe system and associated methods of use will be apparent, particularly when read in conjunction with the appended figure.

BRIEF DESCRIPTION OF THE FIGURE

To assist those of ordinary skill in the art in making and using the disclosed syringe system, reference is made to the accompanying figure, wherein.

DESCRIPTION OF EXEMPLARY EMBODIMENT(S)

As noted above, the present disclosure provides a sterilely packaged syringe that is vacuum-charged prior to removing the syringe from its sterile packaging pouch. By charging a vacuum into the barrel of the syringe within the sterile packaging pouch, the method and system of the present disclosure facilitates desired positioning of the plunger inside the syringe barrel while in an aseptic field, and due to the pre-positioning of the plunger, contamination of the fluid sample that is ultimately drawn into the syringe is advantageously avoided. Once removed from the sterile packaging, the vacuum created within the barrel of the syringe allows the user to automatically and immediately draw fluid into the syringe body by opening up a conduit between the syringe body and the device being sampled.

The advantages associated with the disclosed syringe system and associated method of use are illustrated, at least in part, by the challenges inherent to syringe-based applications in sterile environments. For example, it is noted that typical syringes and stopcock valves do not hold vacuum indefinitely. Thus, it is not possible to package syringe systems in a vacuum-containing orientation, i.e. with the plunger in a pulled back/locked position, "at the manufacturing facility" because, upon receipt in the clinical environment, the vacuum will have been dissipated, in whole or in part, in the vast majority of cases (e.g., loss of 20% vacuum in a single day). Moreover, the unpredictability of the level and reliability of vacuum level in the syringe system would make it impossible for health care providers to rely on syringe systems manufactured/delivered in this way. According to the present disclosure, advantageous syringe systems and methods are provided wherein the syringe system is aseptically packaged without vacuum. The disclosed pouch is generally provided with instructions for the user to actuate the vacuum feature by grasping the syringe plunger and pulling it back while the syringe is still in the pouch and prior to opening the pouch. This will generate a vacuum within the barrel of the syringe on demand while the syringe is still inside the sterile field of the pouch. The locking feature of the syringe is then engaged by rotating the plunger such that a feature on the plunger armature engages a locking point on the syringe barrel, in this case a plastic protrusion designed to engage with the plunger. In this way, a reliable level of vacuum is provided for clinical use.

Figure 1:
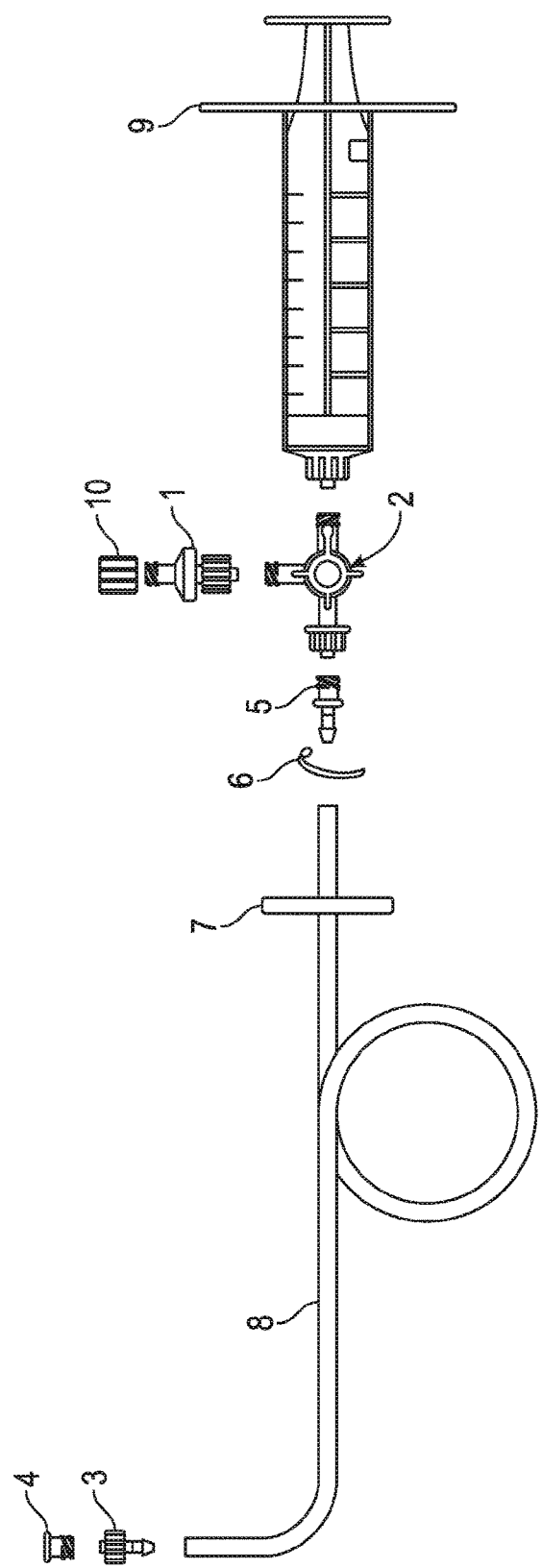
FIG. 1 is a drawing that shows an exemplary syringe system according to the present disclosure.
Figure 2:
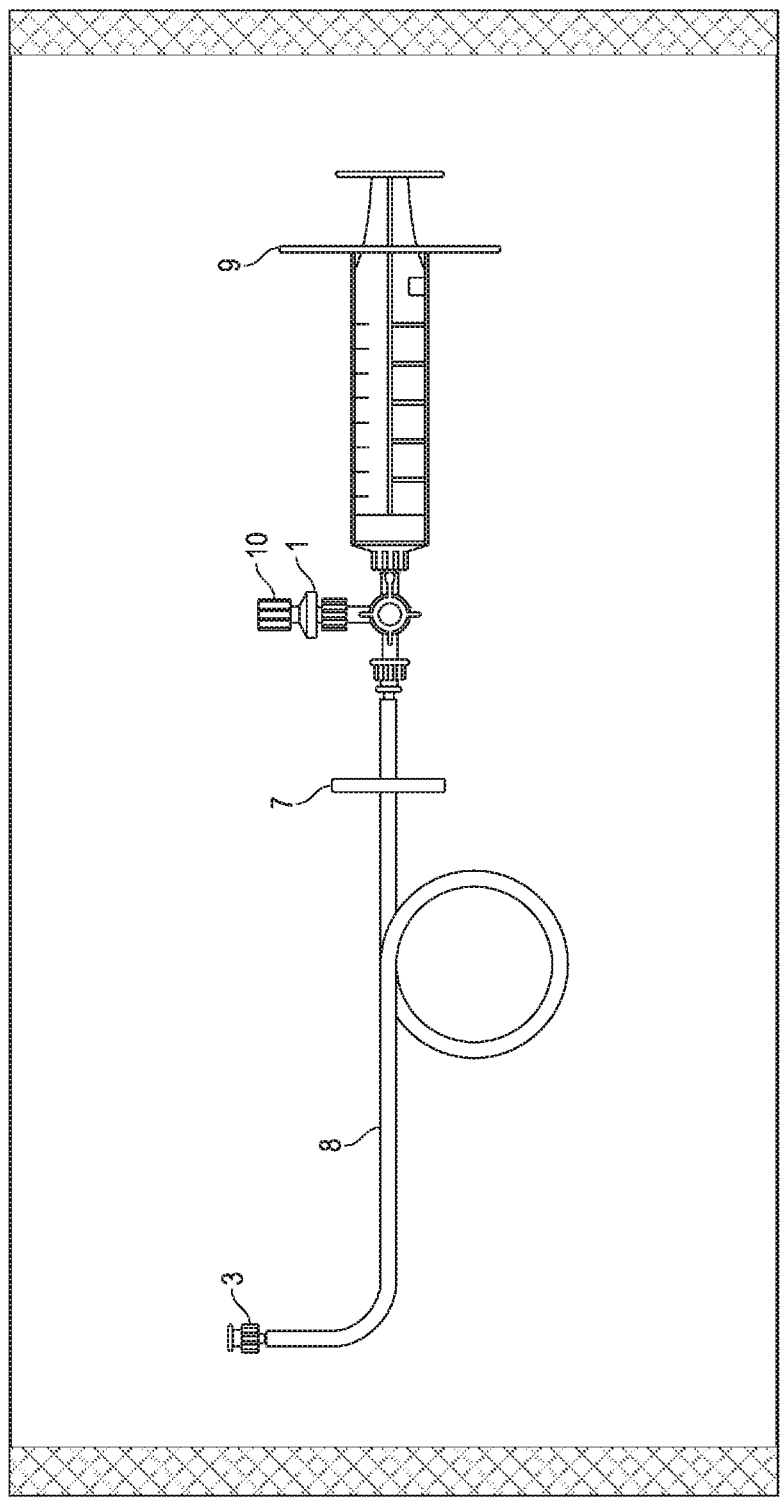
FIG. 2 is a drawing that shows an exemplary syringe system contained within a sealed pouch according to the present disclosure.

With reference to FIG. 1, an exemplary syringe system according to the present disclosure is depicted. As set forth in the bill of materials (lower left corner), the syringe system includes the following:

| Element | Reference Number |
| --- | --- |
| Check valve | 1 |
| 3-way stopcock | 2 |
| Male luer | 3 |
| Female luer cap | 4 |
| Female luer | 5 |
| Cable tie | 6 |

| Element | Reference Number |
| --- | --- |
| Slide clamp | 7 |
| Thermoplastic tubing | 8 |
| Vacuum lock syringe | 9 |
| Cap | 10 |

In exemplary implementations of the present disclosure, the following design elements and design criteria are generally applicable:

1. The syringe is manufactured as indicated in FIG. 1, with respect to the plunger being fully inserted and the "off" switch facing the inlet of the syringe.
2. The system is packaged inside two poly-pouches with enough length in the design of the pouch such that the user can grasp the barrel of the syringe and actuate it by pulling backwards on the plunger, thereby generating a vacuum inside the syringe barrel. The operator ideally performs this procedure at time of use.
3. Once actuated, the syringe is removed from the pouch. The end-user can now connect the device in the following ways:
    A) Tube Welder: connect the system to the device being sampled (typically a bioreactor in cell culture applications) to tube (e.g., C-Flex tubing 8) using an aseptic tubing welder.
    B) Tubing connection: connect the system to the device being sampled using fitting (e.g., male luer 3) on the end of the tubing. Although the exemplary embodiment of FIG. 1 includes a male luer lock type connector, alternative connectors may be employed, e.g., newer aseptic type connectors. Of note, unless an aseptic type connector is used, this step would be a non-closed, or non-aseptic, connection; however, if performed inside a sterile field, such as a laminar flow cabinet equipped with HEPA filters, it could be considered an aseptic step provided appropriate technique is followed.
    C) Syringe Connection: Unscrew the female luer fitting 5 at the base of the tubing and connect the 3-way valve 2 directly to the device being sampled. Again, this is not an aseptic connection unless performed inside a sterile field using proper aseptic technique.
4. Once connected, the user can choose to "flush and sample" (A+B below) or simply take a sample (just B below)
    A) Flush out the sample line: Connect a "flushing syringe" to the inlet of check valve 1 and pull fluid through the check valve into the "flushing syringe". The check valve prevents back flow into the sampling system and device being sampled. Alternatively, the invention could be made such that in lieu of, or addition to, check valve 1, a second vacuum-charged syringe can be pre-connected to this outlet, either directly or with a short length of tubing. This would be done in highly critical applications where the end-user of the system demands that all operations are truly closed and cannot rely on the performance of the check valve to maintain sterility.
    B) Take a fluid sample: Rotate the off switch 90 degrees counter-clockwise such that "Off" is facing the check valve. This will open up the conduit between the syringe barrel (which is under vacuum) and the device being sampled, at which time the fluid will flow from the device being sampled automatically into the syringe.

5. Remove the Syringe: After the sample is collected, the user may actuate slide clamp 7 in order to isolate the syringe from the device being sampled. At this point, the user can:

A) Remove the syringe: Rotate the off-switch 90 degrees clockwise returning it to the starting position; this rotation of the 3-way valve 2 locks the fluid collected into the syringe. The syringe can now be disconnected from the female luer fitting 5.

B) Express residual air, then remove the syringe: In some cases, it may be desirable to remove a small lemon-seed amount of air entrained in the syringe and visible in the syringe barrel. If it is desired to remove air, the off-switch should be rotated another 90 degrees counter-clockwise towards the device being sampled, thus opening up a conduit between the syringe and the check valve. The air can now be expressed out of the syringe. Once complete, the off switch can be rotated 180 degrees clockwise back to the original starting position and the syringe can be safely removed from luer fitting 5.

The syringe system and associated method for use described herein effectively addresses the shortcomings/deficiencies in currently available syringe systems. Beyond the exemplary embodiments described above, at least the following alternative embodiments/approaches are contemplated herein:

In alternative embodiments of the present disclosure, an additional check valve may be included between the 3-way valve 2 and luer fitting 5. A second check valve could advantageously provide further assurance of not contaminating the bioreactor, i.e., the device being sampled. The additional check valve will also reduce the flow rate of the fluid entering the syringe and subsequent foaming and/or bubbles formed would be reduced as well.

In a further alternative embodiment, it is contemplated that a syringe system may be designed/developed that holds vacuum for an extended period, e.g., the shelf life of the product, thereby permitting the syringe system to be packaged with a pre-established vacuum at a desired level within the syringe barrel.

Still further, in an additional alternative embodiment it is contemplated that the syringe is pre-charged with vacuum and packaged inside a pouch or other structure, e.g., preformed rigid tray, which is made from a gas impermeable film/material suitable for "vacuum-packaging". Enclosing the vacuum charged syringe inside a package that also contains a vacuum field will deny the syringe of surrounding atmospheric pressure which would/could cause seepage and degrade the vacuum field inside the syringe. However, this embodiment will add cost and additional manufacturing steps to the product. Further, due to the irregular shape of the syringe there is no guarantee that the vacuum applied to the packaging will be identical for each syringe produced. Moreover, the integrity of the vacuum-stressed film or package now plays an integral part in the successful use of the finished device. For example, if film/material of the package is punctured, the syringe will see a measureable loss in the vacuum. Non-sterile ambient air will enter the packaging environment and degradation of vacuum quality will occur as previously described.

Although the present disclosure has been described with reference to exemplary embodiments/implementations thereof, the present disclosure is not limited by or to such exemplary embodiments/implementations. Rather, the present disclosure is susceptible to many variations, modifications and/or refinements without departing from the spirit or scope of the present disclosure, as will be readily apparent to persons skilled in the art from the description provided herein.

The invention claimed is:

1. A method for sampling fluids, comprising:
providing a syringe system positioned within a packaging pouch in a sterilized condition, the syringe system including (i) a vacuum lock syringe that includes a syringe barrel and a plunger movably positioned relative to the syringe barrel, and (ii) a 3-way valve mounted with respect to the syringe system;
pulling the plunger back within the syringe barrel so as to establish a vacuum within the syringe barrel with the syringe system positioned within the packaging pouch in the sterilized condition; and
withdrawing the syringe system from the packaging pouch with the vacuum established within the syringe barrel; and
sampling a fluid by connecting the syringe system with respect to a fluid-containing device to be sampled.

2. The method according to claim 1, wherein the syringe system further includes a check valve mounted with respect to the 3-way valve.

3. The method according to claim 1, further comprising a luer fitting mounted with respect to the 3-way valve.

4. The method according to claim 3, further comprising a check valve positioned between the luer fitting and the 3-way valve.

5. The method according to claim 1, wherein the fluid sample is drawn into the syringe barrel without compromising sterility thereof.

6. The method according to claim 1, further comprising a flushing step wherein a flushing syringe is connected to an inlet of a check valve associated with the 3-way valve and fluid is drawn into the flushing syringe through the 3-way valve and the check valve.

\* \* \* \* \*